(12) United States Patent
Jordan et al.

(10) Patent No.: US 10,183,418 B2
(45) Date of Patent: Jan. 22, 2019

(54) DYNAMIC SEGREGATION MONITORING OF CONCRETE

(71) Applicant: VERIFI LLC, Cambridge, MA (US)

(72) Inventors: Richard K. Jordan, Littleton, MA (US); Mark F. Roberts, North Andover, MA (US); Yan Glina, Medford, MA (US); Nathan A. Tregger, Northborough, MA (US); Lawrence R. Roberts, Acton, MA (US); Eric P. Koehler, Miami Beach, FL (US)

(73) Assignee: VERIFI LLC, Cambridge, MA (US)

( * ) Notice: Subject to any disclaimer, the term of this patent is extended or adjusted under 35 U.S.C. 154(b) by 219 days.

(21) Appl. No.: 15/302,901

(22) PCT Filed: Apr. 9, 2015

(86) PCT No.: PCT/US2015/025054
§ 371 (c)(1),
(2) Date: Oct. 7, 2016

(87) PCT Pub. No.: WO2015/160610
PCT Pub. Date: Oct. 22, 2015

(65) Prior Publication Data
US 2017/0028586 A1 Feb. 2, 2017

Related U.S. Application Data

(60) Provisional application No. 61/979,217, filed on Apr. 14, 2014.

(51) Int. Cl.
*G05B 21/00* (2006.01)
*B28C 5/42* (2006.01)
(Continued)

(52) U.S. Cl.
CPC .............. *B28C 5/422* (2013.01); *B28C 7/026* (2013.01); *E01C 19/1027* (2013.01);
(Continued)

(58) Field of Classification Search
CPC ...................................................... B28C 5/422
(Continued)

(56) References Cited

U.S. PATENT DOCUMENTS 5,713,663 A 2/1998 Zandberg et al.
5,752,768 A 5/1998 Assh
(Continued)

FOREIGN PATENT DOCUMENTS

WO 2013144528 10/2013

OTHER PUBLICATIONS

Lee, H. K., et al. "Ultrasonic in-situ monitoring of setting process of high-performance concrete." Cement and Concrete Research 34.4 (2004): pp. 631-640. (Year: 2004).*
(Continued)

*Primary Examiner* — Satish Rampuria
(74) *Attorney, Agent, or Firm* — Craig K. Leon (57) ABSTRACT

A system and process for detecting dynamic segregation in concrete rotated within a mixer drum, such as mounted on a delivery truck. A system processor is programmed to monitor an instantaneous and averaged rheology parameter and to deploy protocols for detecting segregation. A first protocol comprises monitoring the averaged slump during and immediately after a jump in drum speed of at least plus or minus four rotations per minute and detecting when a change in the averaged slump value meets or exceeds a threshold; and a second protocol comprises monitoring the instantaneous slump when the mixer drum is rotating at a constant speed for at least three successive rotations and detecting when the instantaneous slump value meets or
(Continued)

exceeds a threshold limit. Once segregation is detected, one or more operations can be initiated, such as initiating an alarm or adjusting the mix.

28 Claims, 7 Drawing Sheets

(51) Int. Cl.
  *B28C 7/02* (2006.01)
  *E01C 19/10* (2006.01)
  *G05B 19/048* (2006.01)
(52) U.S. Cl.
  CPC ........ *E01C 19/1063* (2013.01); *G05B 19/048* (2013.01); *G05B 2219/42286* (2013.01)
(58) Field of Classification Search
  USPC .................................................. 700/245–306
  See application file for complete search history.

(56) References Cited

U.S. PATENT DOCUMENTS

| | | | |
|---|---|---|---|
| 8,020,431 B2 | 9/2011 | Cooley et al. | |
| 8,118,473 B2 | 2/2012 | Compton et al. | |
| 8,311,678 B2 | 11/2012 | Koehler et al. | |
| 8,491,717 B2 | 7/2013 | Koehler et al. | |
| 8,764,272 B2 * | 7/2014 | Hazrati | B28C 7/026 366/142 |
| 8,764,273 B2 * | 7/2014 | Koehler | B28C 5/08 366/8 |
| 8,960,990 B2 * | 2/2015 | Koehler | B28C 7/026 366/61 |
| 9,952,246 B2 * | 4/2018 | Jordan | G01C 19/02 |
| 2007/0185636 A1 | 8/2007 | Cooley et al. | |
| 2008/0316856 A1 | 12/2008 | Cooley et al. | |
| 2009/0037026 A1 | 2/2009 | Sostaric et al. | |
| 2010/0312438 A1 | 12/2010 | Cooley et al. | |
| 2011/0029134 A1 | 2/2011 | Hazrati et al. | |
| 2012/0016523 A1 | 1/2012 | Koehler et al. | |
| 2012/0020180 A1 | 1/2012 | Koehler et al. | |
| 2017/0028586 A1 * | 2/2017 | Jordan | B28C 7/026 |

OTHER PUBLICATIONS

Jo, Byung-Wan, et al. "Characteristics of cement mortar with nano-SiO2 particles." Construction and building materials 21.6 (2007): pp. 1351-1355. (Year: 2007).*

Khayat, Kamal H. "Workability, testing, and performance of self-consolidating concrete." Materials Journal 96.3 (1999): pp. 346-353. (Year: 1999).*

Voltz, Supplementary European Search Report, Application No. EP15780355, dated Dec. 1, 2017, 9 pages.

Copenheaver, From PCT/ISA/210, International Search Report, International Application No. PCT/US2015/025054, 3 pages, dated Jul. 1, 2015.

Copenheaver, From PCT/ISA/237, Written Opinion of the International Searching Authority, International Application No. PCT/US2015/025054, 12 pages, dated Jul. 1, 2015.

* cited by examiner

DYNAMIC SEGREGATION MONITORING OF CONCRETE

FIELD OF THE INVENTION

The present invention relates to manufacture and processing of concrete, and more particularly to a monitoring system and process for confirming existence of dynamic segregation in concrete contained in mixer drums such as found on concrete delivery trucks.

BACKGROUND OF THE INVENTION

It is known to employ automated systems and processes for monitoring slump and other properties of concrete contained in rotating mixer drums, such as mixer drums that are mounted on concrete delivery trucks. The hydraulic pressure required to rotate the concrete in the mixer drum can be measured by a processor unit on a continuous basis and correlated with the property of the concrete being mixed, and adjustments can be made to the concrete through additions of water or chemical as controlled by the automated system processor unit.

In US 2012/0020180 A1 (owned by the same assignee hereof), Koehler et al. taught that variations in the energy or hydraulic pressure monitored during successive instances during rotation of the mixer drum could be compared by a processor unit with stored variations in the energy or hydraulic pressure as previously derived by the processor unit during successive instances of drum rotation. Thus, it is claimed that segregation and other properties of the concrete can be monitored by examining slight changes in energy or hydraulic pressure expended per drum rotation over time.

Segregation is present when the cement paste matrix no longer holds the aggregate together uniformly within the fluid volume of the mix, and separation of the aggregate from the cement paste occurs. In ASTM C125-11, the term "segregation" is defined as the "unintentional separation of the constituents of concrete or particles of an aggregate, causing a lack of uniformity in their distribution." Such separation may occur while the concrete is being moved, so-called "dynamic segregation," and separation may also occur in the quiescent state when the concrete is not being agitated or mixed, and this is otherwise called "static segregation."

Improper aggregate grading, aggregate shape, and other factors may cause concrete to become segregated, and such factors may arise outside of the knowledge of the concrete manufacturer. Segregation can cause the concrete to be rejected at the job site, or, if such a segregated concrete is poured and placed at the job site, the hardened concrete is likely to result in a weak, porous, and non-durable structure. In serious cases, concrete that has segregated but has been placed will need to be removed and replaced, causing job delays and cost increases. If the materials are known in advance to be susceptible to this problem, the mix designer can exercise greater care in selection and proportioning of ingredients, but day-to-day variations in raw material and mixing behavior can result in undetected segregation occurrences and serious consequences.

It is an objective of the present invention to improve dynamic segregation monitoring by providing specific protocols for detecting and confirming the existence of this condition such that adjustments to the concrete and other actions can be taken.

SUMMARY OF THE INVENTION

In surmounting the disadvantages of the prior art, the present invention provides a system and method for monitoring dynamic segregation in concrete that is contained in rotatable mixer drums, such as those which are used on concrete delivery trucks. The mixer drums have an inner wall with at least one blade, and more preferably two blades, spirally-mounted on the inner wall for agitating or mixing the concrete during rotation.

An exemplary concrete monitoring system of the present invention comprises:

at least one processor that is programmed to monitor at a rate of at least ten times per drum rotation at least one rheology parameter of concrete contained in a rotating drum by measuring the energy or hydraulic pressure required for rotating the concrete-containing drum as a function of time and thereby to obtain an instantaneous value for the rheology parameter (hereinafter "instantaneous rheology value"), the processor being further programmed to average the monitored rheology values for the rheology parameter in question over a period of time to obtain an averaged value for the rheology parameter (hereinafter "averaged rheology value"); the system processor being further programmed to deploy a first dynamic segregation detection protocol, and optionally to deploy a second dynamic segregation detection protocol, wherein (A) the first dynamic segregation detection protocol comprises: monitoring the concrete rheology parameter before and after drum rotation is detected to jump from a first constant rotation speed to a second constant rotation speed, wherein the difference between the first and second rotation speeds is at least plus or minus four drum rotations per minute; and, upon completion of the jump, detecting when a change in the averaged rheology value meets or exceeds a Jump Speed Departure Value that is pre-selected with respect to the monitored averaged rheology value (hereinafter "JSDV(A) limit"); and, optionally, the first dynamic segregation detection protocol further comprises detecting when a change in the instantaneous rheology value meets or exceeds a Jump Speed Departure Value preselected with respect to the monitored instantaneous rheology value (hereinafter "JSDV(I) limit");

(B) the second dynamic segregation detection protocol comprises: monitoring the concrete while the mixer drum is rotating at a constant rotation speed and detecting when a change in the monitored instantaneous rheology value meets or exceeds a Constant Speed Departure Value (hereinafter "CSDV limit"); and the system processor being further programmed, upon or after detecting that at least the JSDV(A) limit is met or exceeded, to initiate at least one of the following operations: (i) sending of an alarm or indication to a concrete mix plant, a dispatch center, an operator of the concrete delivery truck, or to some or all of these, to confirm that segregation is detected; (ii) changing of mixer drum rotation rate; (iii) introducing at least one chemical admixture into the concrete-containing mixer drum for mitigating segregation of the concrete; (iv) transmitting of data to a dispatch center, concrete mix plant, or other remote site for adjusting concrete mix design in subsequent concrete batches; or (v) performing any combination or all of the foregoing.

In further exemplary embodiments, the concrete monitoring system preferably implements both first and second dynamic segregation detection protocols. The first and second protocols can be implemented in any order, and the speed jump can be done using a transition from lower to higher speed or from higher to lower speed. Similarly, the constant speed monitoring in the second protocol can occur at any speed, whether high or low or somewhere between.

Accordingly, an exemplary process of the present invention for detecting dynamic segregation in a concrete mix contained in a rotatable mixer drum mounted on a concrete delivery truck, the drum having an inner wall with at least one blade spirally-mounted on the inner wall for agitating or mixing the concrete during rotation, comprises:

monitoring at a rate of at least ten times per drum rotation at least one rheology parameter of concrete contained in a rotating drum by measuring the energy or hydraulic pressure required for rotating the concrete-containing drum as a function of time and thereby obtaining instantaneous values for the rheology parameter (hereinafter "instantaneous rheology values"), and averaging the monitored rheology values for the rheology parameter in question over a period of time to obtain an averaged value for the rheology parameter (hereinafter "averaged rheology value");

implementing a first dynamic segregation detection protocol, and, optionally, a second dynamic segregation detection protocol, wherein (A) the first dynamic segregation detection protocol comprises: monitoring the concrete rheology parameter before and after drum rotation is detected to jump from a first constant rotation speed to a second constant rotation speed, wherein the difference between the first and second rotation speeds is at least plus or minus four drum rotations per minute; and, upon completion of the jump, detecting when a change in the averaged rheology value meets or exceeds a Jump Speed Departure Value that is pre-selected with respect to the monitored averaged rheology value (hereinafter "JSDV(A) limit"); and, optionally, detecting when a change in the instantaneous rheology values meets or exceeds a Jump Speed Departure Value preselected with respect to the monitored instantaneous rheology values (hereinafter "JSDV(I) limit");

(B) the second dynamic segregation detection protocol comprising: monitoring the concrete while the mixer drum is rotating at a constant rotation speed and detecting when variations in the monitored instantaneous rheology values meet or exceed a Constant Speed Departure Value (hereinafter "CSDV limit"); and initiating at least one of the following upon or after confirming that at least the JSDV(A) limit is met or exceeded: (i) sending an alarm or indication or both to the concrete mix plant, a dispatch center, an operator of the concrete delivery truck, or to some or all of these, to confirm that segregation is detected; (ii) changing the mixer drum rotation rate; (iii) introducing at least one chemical admixture into the concrete-containing mixer drum for mitigating segregation of the concrete; (iv) transmitting of data to a dispatch center, concrete mix plant, or other remote site, to facilitate adjustment of the concrete mix design or preparation to avoid segregation in subsequent concretes in the mixer drum; or (v) performing any combination or all of the foregoing. Preferably, both protocols are implemented to confirm that dynamic segregation is detected, and that both JSDV(A) and CSDV limits are met or exceeded. As previously mentioned, these functions can be performed regardless of whether the jump in mixer drum speed is from lower to higher or from higher to lower speed, or whether the constant speed monitoring is done at high or low speed.

The concept of "jump speed" or jump in the mixer drum rotation speed, as used herein, shall mean and refer to a sudden change in concrete mixer drum rotation from a first constant rotation speed to a second constant rotation speed wherein the difference between first and second speeds are at least plus or minus four (4) drum rotations per minute (RPM). The concept of "constant speed" or "constant rotation speed," as used herein, refers to the speed of a concrete mixing drum that has been rotated at a fixed rate of rotation for at least three complete drum revolutions, and, more preferably, for at least five complete drum revolutions, without varying by more than 0.5 drum rotations per minute (RPM).

Thus, the present invention concerns the use of the system processor to employ at least one protocol, and preferably two different protocols, for detecting (and confirming) dynamic segregation as it occurs in real time within the concrete mix contained in a rotating drum. The JSDV and CSDV limits are preferably derived by the system processor based on concrete mix design and materials, temperature of the concrete, admixtures introduced into the concrete, past and current delivery performance and other variables; although both or either of the JSDV and CSDV may be pre-selected by the operator of the system and/or truck or inputted by an operator located at a remote dispatch center, although these options are less preferred.

The present invention is best practiced by modification to concrete monitoring systems commercially available from Verifi LLC of Ohio, an affiliate of Grace Construction Products (Massachusetts). The Verifi® slump monitoring systems typically employ sensors for measuring effort (e.g. hydraulic pressure, work, torque, energy, etc.) required to mix an enclosed volume of concrete and at least one processor to execute various management algorithms (and detection procedures as will be described further herein). The processor may be an embedded microprocessor, or perhaps a micro-controller or digital signal processor installed on-board the concrete delivery truck. Alternatively, the computer processor may be located remotely, such as at concrete batch plant, data center, IT services company), or other location (not on the mixing truck) that is convenient for data processing. In any event, the computer processor is hereinafter referred to as the processor or system processor. The Verifi® systems also employ networking components which can used be in wired or wireless configuration to communicate sensor information to the system processor. Finally, the Verifi® systems also employ fluid management equipment such as valves, actuators, pressurization equipment, tanks, pumps, hoses, etc., for introducing liquids into the concrete mixer drum.

While automated concrete monitoring systems are known for monitoring slump, it will be understood that the present invention is applicable during the monitoring of other rheology parameters, including slump, slump flow, yield stress, viscosity, and other rheological parameters. The term "slump" may be used in the present specification to illustrate conveniently any of these rheology parameters; and it should be understood that present invention covers the monitoring of other rheology parameters even when "slump" is indicated.

Further advantages and features of the present invention may be described in detail hereinafter.

BRIEF DESCRIPTION OF DRAWINGS

An appreciation of the benefits and features of the present invention may be more readily comprehended by considering the following written description of preferred embodiments in conjunction with the drawings, wherein.

DETAILED DESCRIPTION OF PREFERRED EMBODIMENTS

The present invention now will be described more fully hereinafter with reference to the accompanying drawings, in which various exemplary embodiments are shown illustrating variations within the scope of the invention. This disclosure may, however, be embodied in many different forms and should not be construed as limited to the embodiments set forth herein; rather, these embodiments are provided so that this disclosure will be thorough and complete and fully convey the scope of the invention to those of ordinary skill in the art.

The term "cement" as used herein includes hydratable cement such as Portland cement which is produced by pulverizing clinker consisting of hydraulic calcium silicates, aluminates and aluminoferrites, and one or more forms of calcium sulfate (e.g., gypsum) as an interground additive. Portland cement may be combined with one or more supplemental cementitious materials, such as fly ash, granulated blast furnace slag, limestone, natural pozzolans, or mixtures thereof, and provided as a blend. Thus, "cement" may also include supplemental cementitious materials which have been inter-ground with Portland cement during manufacture. The term "cementitious" may be used herein to refer to materials that comprise Portland cement or which otherwise function as a binder to hold together fine aggregates (e.g., sand), coarse aggregates (e.g., crushed gravel), or mixtures thereof, in mortar and concrete.

The term "hydratable" as used herein is intended to refer to cement or cementitious materials that are hardened by chemical interaction with water. Portland cement clinker is a partially fused mass primarily composed of hydratable calcium silicates. The calcium silicates are essentially a mixture of tricalcium silicate ($3CaO \cdot SiO_2$ or "$C_3S$" in cement chemists' notation) and dicalcium silicate ($2CaO \cdot SiO_2$, "$C_2S$") in which the former is the dominant form, with lesser amounts of tricalcium aluminate ($3CaO \cdot Al_2O_3$, "$C_3A$") and tetracalcium aluminoferrite ($4CaO \cdot Al_2O_3 \cdot Fe_2O_3$, "$C_4AF$"). See e.g., Dodson, Vance H., *Concrete Admixtures* (Van Nostrand Reinhold, New York, N.Y. 1990), page 1.

The term "concrete" thus typically refers to hydratable cementitious mixtures comprising cement, sand, and usually a coarse aggregate such as crushed stone or gravel, and optionally one or more chemical admixtures. Chemical admixtures are added to concrete for purposes of modifying any number of properties, including, by way of example, reducing the need for water (e.g., plasticizing, increasing workability), controlling the setting of concrete (e.g., set accelerating, set retarding), managing air content and quality (e.g., air entraining agents, air detraining agents), shrinkage reduction, corrosion inhibition, and other properties.

Figure 1:
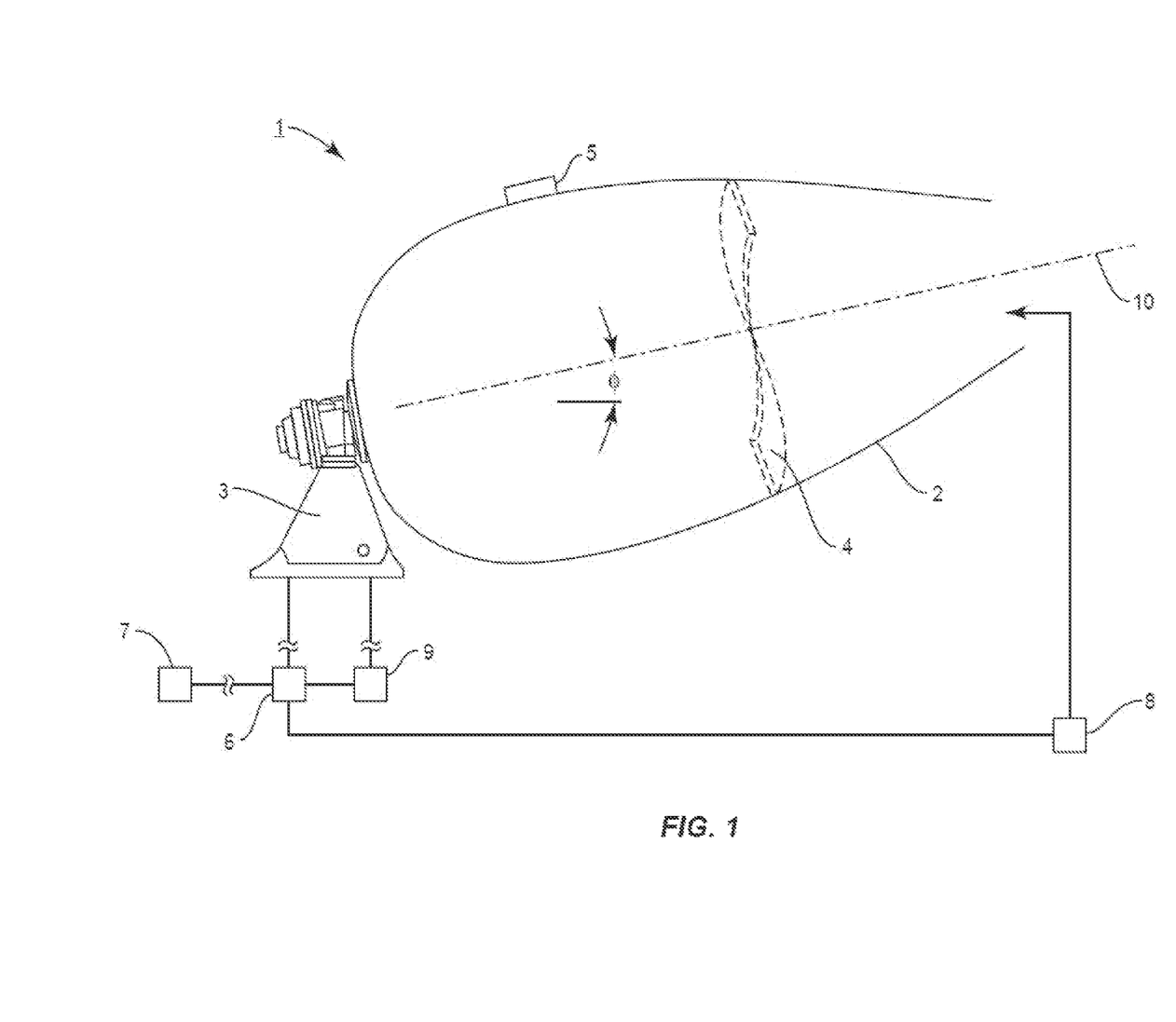
FIG. 1 is a diagrammatic illustration of an automated slump monitoring system used for monitoring the rheology (e.g., slump) of a concrete mix in a rotatable concrete mixer drum, wherein the system has a processor unit that can be programmed to accomplish detection and confirmation of a dynamic segregation state in the concrete mix in accordance with the teachings of the present invention.

As shown in FIG. 1, an exemplary system 1 of the present invention can be obtained by modifying (by way of software programming) automated concrete monitoring systems which have a rotatable concrete mix drum 2 which is driven by a motor 3 which can be powered by electric drive, or, more preferably, by hydraulic pressure. In concrete ready-mix delivery trucks (the truck frame is not shown), the mixer drum 2 has an internal wall upon which are spirally-mounted (with respect to the rotational axis of the drum 2 designated by the dashed/dotted line at 10 which is oriented at angle Ø with respect to horizontal ground) at least one mixing blade 4, and more preferably two mixing blades, such that when the mixer drum 2 is rotated in a first direction the contents of the drum are pushed towards the closed end of the drum and are thus mixed; and such that when the mixer drum 2 is rotated in a second, opposite direction the contents are expelled by the at least one spirally-mounted mixing blade 4 toward the drum opening and discharged from the mixer drum 2. A processor unit (designated as at 6) is electrically or wirelessly connected to the motor/drive 3 and to a sensor (designated as at 9) connected to the motor/drive 3 so that the processor unit 6 can monitor the energy or hydraulic pressure required to rotate the drum 2 at a given speed. The processor unit 6 is electrically or electronically connected to one or more memory locations (designated as at 7) which can be used for storing program applications for monitoring the speed of the motor/drive 3 and hence for monitoring the rheological property (e.g., slump) of the concrete in the mixer drum 2. The processor unit 6 can also be electrically and/or electronically connected to one or more dispensing systems (such as the one represented as at 8) for administering water, chemical admixtures, or both, into a concrete mix contained in the mixer drum 2. The dispensing system 8 can comprise one or more separate tanks for transporting and dispensing one or more fluids (chemical admixtures, water, etc.).

In preferred embodiments, automated concrete monitoring systems of the present invention comprise at least one processor 6 and at least one hydraulic sensor 9 for tracking the energy or hydraulic pressure required to rotate a concrete mix in the mixer drum 2, and a sensor for measuring the rotation speed of the drum 2. The processor unit designated at 6 may incorporate (or be integrated with) one or more receiver units for receiving signals from various sensors (and transmitters) located on the truck, as well as one or more transmitters for transmitting signals to receivers and further processor units located elsewhere (such as at the concrete plant, the dispatch center, the laptop of the project manager, etc.).

As an example, a speed sensor can comprise a series of magnets mounted on the drum and configured to pass by one or more magnetic sensor(s) on the truck to create a signal each time the magnet passes the magnetic sensor, thereby permitting the rotational speed, turning direction, and number of rotations to be monitored (See e.g., U.S. Pat. No. 5,752,768 of Assh). Alternatively, the rotational sensor may be incorporated in the driving motor 3 or other hydraulic motors and pumps. As a third potential embodiment, the rotational speed sensor may be an integrated accelerometer mounted on the drum of the concrete truck, as designated at 5 in FIG. 1, which is coupled to a wireless transmitter which transmits a signal from the accelerometer to a processor unit (which can be on-board the truck such as designated at 6) from which can be determined the rotational speed of the drum 2. An accelerometer is described in U.S. Publication No. 2012/0004790 A1 (U.S. Ser. No. 13/236,433) of Roy Cooley et al., which is owned by the common assignee hereof. An integrated accelerometer/gyroscope module is commercially available from Verifi LLC of West Chester, Ohio, USA, which provides for wireless transmission of drum speed data to onboard processor or remotely located processors. The module contains an accelerometer, gyroscope, wireless transmitter, battery pack, and microprocessor programmed for data collection and other functions, such as monitoring of the inclination of the drum.

The system and method of the present invention for monitoring dynamic segregation of concrete within a mixing drum can be achieved by specific programming and calibration, as will be further explained in detail herein, of available automated concrete monitoring systems. As summarized above, systems that can be modified to fulfill the objectives of the present invention are commercially available from Verifi, LLC, of Ohio. These are designed for use on concrete ready-mix delivery trucks whose mixer drums are rotated using hydraulic pressure, but they could be readily adopted for mixer drums rotated using other means (e.g., electrical). The general concepts behind the automated monitoring systems are variously outlined or otherwise explained in the patent literature, such as: See e.g., U.S. Pat. No. 8,118,473 to Compton et al.; U.S. Pat. No. 8,020,431 to Cooley et al.; U.S. Pat. No. 8,491,717 to Koehler et al.; U.S. Ser. No. 10/599,130 to Cooley et al. (Publication No. US 2007/70185636 A1); U.S. Ser. No. 11/834,002 to Sostaric et al. (Publication No. US 2009/0037026 A1); and US Serial No. 258,103 to Koehler et al. (Publication No. 2012/0016523 A1).

At a minimum, the concrete monitoring systems and methods of the invention should comprise at least one processor (as designated at 6 and/or contained in an integrated accelerometer module as designated at 5); at least one sensor for monitoring the energy or hydraulic pressure required to rotate the mixer drum (e.g., and, more preferably, at least two hydraulic pressure sensors, one installed in the charge port and a second installed in the discharge port of the motor used for rotating the mixer drum where it is desired to measure both charging pressure and discharging pressure); a speed sensor or sensor device for measuring mixer drum speed (e.g., number of drum rotations per time period) such as one of the speed sensors previously discussed above; preferably, a device for dosing water and/or chemical admixture 8 into a concrete mix in the drum 2 as controlled by the at least one processor; and processor-accessible memory for storing instructions relative to dynamic segregation detection protocols in accordance with the present invention.

As previously mentioned, it is understood that while "slump" may be used as an example of one kind of rheological property that can be monitored and controlled using available automated monitoring systems, and adapted for use in monitoring segregation in accordance with the present invention. The rheology being monitored by the system processor can also include "slump flow" as well as other rheological properties such as yield stress, viscosity, or others. For example, in U.S. Ser. No. 13/258,104 as published in Publication No. 2012/00166523 A1 (owned by the common assignee hereof), Koehler et al. described how an automated monitoring system that was calibrated for monitoring concrete slump (measured using vertical slump cone test described in ASTM C143-05) could be modified to monitor concrete slump flow (measured using horizontal spread test described in ASTM C1611-15) and thus enable capabilities not before recognized within the concrete industry.

As shown in the diagram of FIG. 1 which illustrates an automated concrete monitoring system as may be installed on a ready-mix concrete delivery truck, at least one processor unit such as designated in FIG. 1 at 6 is programmed to perform the following functions: for example, the processor unit 6 follows a set of instructions which may be stored in memory 7 to monitor a rheology parameter (e.g., slump, slump flow, yield stress, viscosity) of the concrete mix in a non-segregated state over a period of time and to record variations in the recorded rheological behavior during this period at different mixer drum 2 rotation speeds. In exemplary embodiments of the present invention, the system processor 6 is programmed to monitor, at a rate of at least 10 times per drum rotation or more (and more preferably at least 20-25 times per drum rotation, and most preferably at least 50-100 times or more per drum rotation), the rheology parameter at a given point in time (hereinafter the "instantaneous rheology value," such as, e.g., "instantaneous slump value,") and also programmed to average the monitored values for the rheology parameter in question over a period of time to obtain an averaged value for the rheology parameter in question (hereinafter the "averaged rheology value," such as, e.g., "averaged slump value,").

The system processor is programmed, for example, to monitor both an instantaneous slump value and averaged slump value (or other rheology value such as slump flow in the alternative or in combination with slump). For purposes of the present invention, the system processor is also programmed to monitor the rheology value for variability upon and immediately after "jump speed" changes as well as during "constant speed." The concept of "constant speed" or "constant rotation speed" as used herein refers to the rotation speed of the drum which has remained constant (less than plus or minus 0.5 RPM variation and more preferably less than plus or minus 0.25 RPM variation) over at least three (and more preferably at least five) successive drum rotations, and, for purposes of the present invention, the instantaneous rheology (e.g., slump) value of the concrete is monitored for at least three (and more preferably at least five) successive rotations. On the other hand, the concept of "jump speed" as used herein refers to a change of at least four rotations per minute (plus or minus 4.0 RPM), and more preferably a change in speed of at least 6 rotations per minute (plus or minus 6.0 RPM), and most preferably a change in speed of at least eight rotations per minute (plus or minus 8.0 RPM), whereby the rotational speed of the drum is suddenly increased or decreased, and, for purposes of the present invention, the averaged rheology (e.g., slump) value and optionally the instantaneous rheology value of the concrete is monitored by the system processor throughout the duration of the jump speed change and for at least three complete rotations (and more preferably at least five complete rotations) from the moment that the speed of the drum was adjusted (by the driver or system processor). This jump speed change can be performed such as by having the concrete truck driver manually effectuate a quick step change to the motor or hydraulic pressure drive which rotates the concrete mixer drum. In some mixing trucks, this can be done by manipulating a lever which controls the speed of the drum. Alternatively, the processor can be configured to control a switch or potentiometer to control the motor or hydraulic pressure drive so as to change the drum speed.

Ready-mix delivery trucks typically employ a "mixing" speed above 12 RPM when first mixing together the components to make the concrete, such as at the batch plant, or after dosing water or chemical admixture into the mix, and also before the discharge or pouring event to ensure that the components are fully mixed when placed; and they also typically use a lower "agitation" speed of 1-6 RPM (and more typically 2-3 RPM) for the predominant portion of the transit period between initial batching at the plant and final delivery at the construction site. It is understood that the "jump speed" and "constant speed" protocols described for the present invention herein can involve monitoring of the concrete within "agitation" or "mixing" speed ranges alone or otherwise involve rotational speeds in between these typical ranges. However, for purposes of the "jump speed" protocol, it is preferred to use a large jump between constant rotation speeds (e.g., at least plus or minus four RPM difference and more preferably plus or minus 6 RPM difference or more); and so it is more likely that jump speed changes will involve quick changes from "agitation" speeds to the higher "mixing" speeds, or vice-versa.

It is also preferred that the jump speed and constant speed monitoring and detection steps be performed when the concrete delivery truck itself is either stationary or travelling at relatively constant speed on level road, because variations of load on the truck engine could adversely affect the constancy of the motor or hydraulic pressure drive used for rotating the mixer drum.

As will be explained in further detail below, the specific use of both the "jump speed" and "constant speed" terminology and their respective meanings are important to understand in connection with exemplary systems and methods of the present invention for monitoring and detecting dynamic segregation states within concrete.

Figure 2:
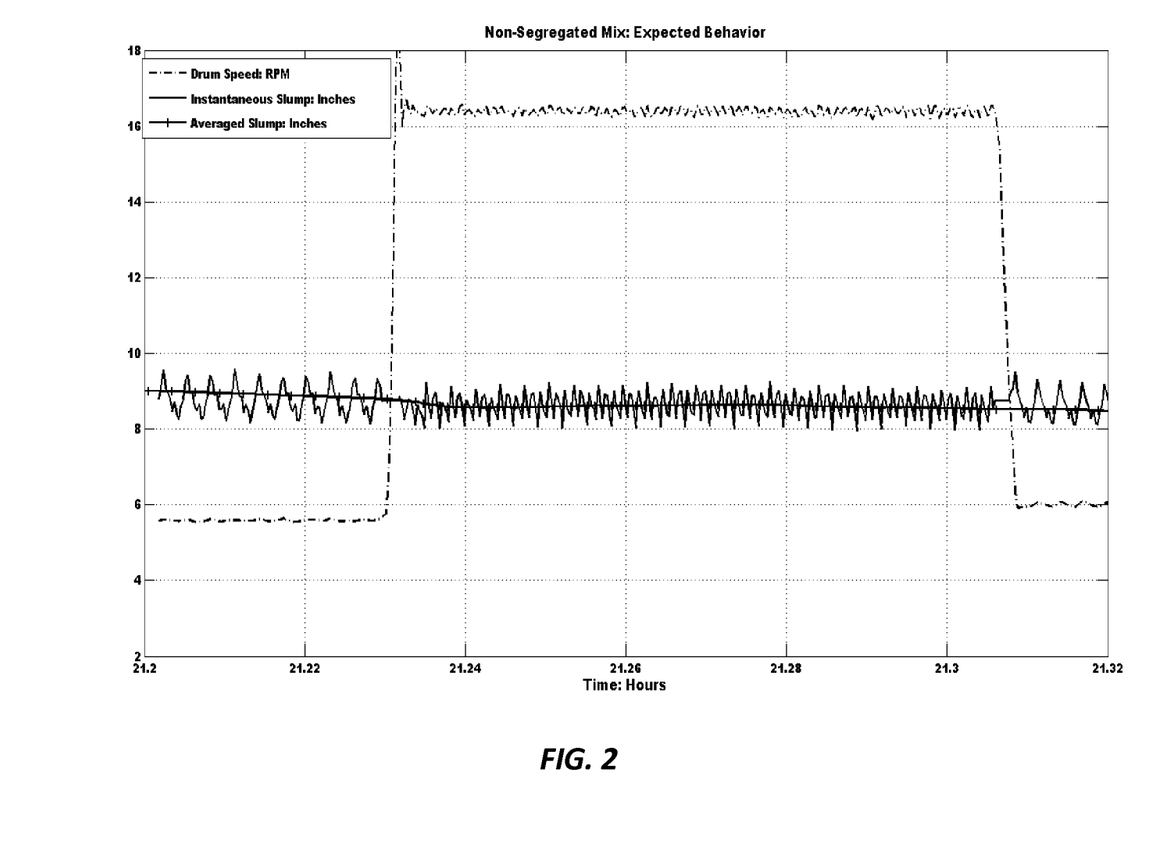
FIG. 2 is a graphic illustration of the "instantaneous" slump (inches) and "averaged slump (inches)" behavior of a non-segregating concrete mix, wherein the rotational drum speed, depicted as a dashed/dotted line indicating rotations per minute or "RPM" shown along the vertical axis is increased from a lower rotational speed to a higher rotational speed and then returned to a lower rotational speed, and further wherein instantaneous and averaged slump behavior is displayed across time (hours) shown along the horizontal axis.

As shown in FIG. 2, an exemplary automated slump monitoring system is programmed to monitor the slump of a non-segregated concrete in a rotatable concrete mixer drum of a concrete delivery truck having a hydraulic system for rotating the drum. The slump value is calculated from the measured energy or hydraulic pressure required to rotate concrete at a certain drum rotational speed. The system processor unit is programmed to monitor and to record into memory the "instantaneous slump (inches)" which is calculated from the energy or hydraulic pressure sensed at a given point in time by the hydraulic pressure sensor at a given drum speed; and the processor unit is also programmed to monitor and to record into memory the "averaged slump (inches)" which is calculated from the energy or hydraulic pressure value as averaged over a brief period of time or within a mixer drum rotation (or portion thereof).

The instantaneous slump of the non-segregated concrete is illustrated in FIG. 2 as a relatively regular periodic wave; while averaged slump of the non-segregated concrete is illustrated in FIG. 2 as a relatively horizontal line within a given time period during which the rotational speed of the drum is held at constant speed. Also as shown in FIG. 2, the non-segregated concrete is rotated at an agitation speed (which is indicated as about 5.6 drum rotations per minute), then rotated for a couple of minutes at a higher "mixing" speed (about 16.3 drum rotations per minute), and then decreased to agitation speed. The graph representing each of the instantaneous and averaged slump values appears uniform with only relatively small variations for each time period shown in FIG. 2.

Figure 3:
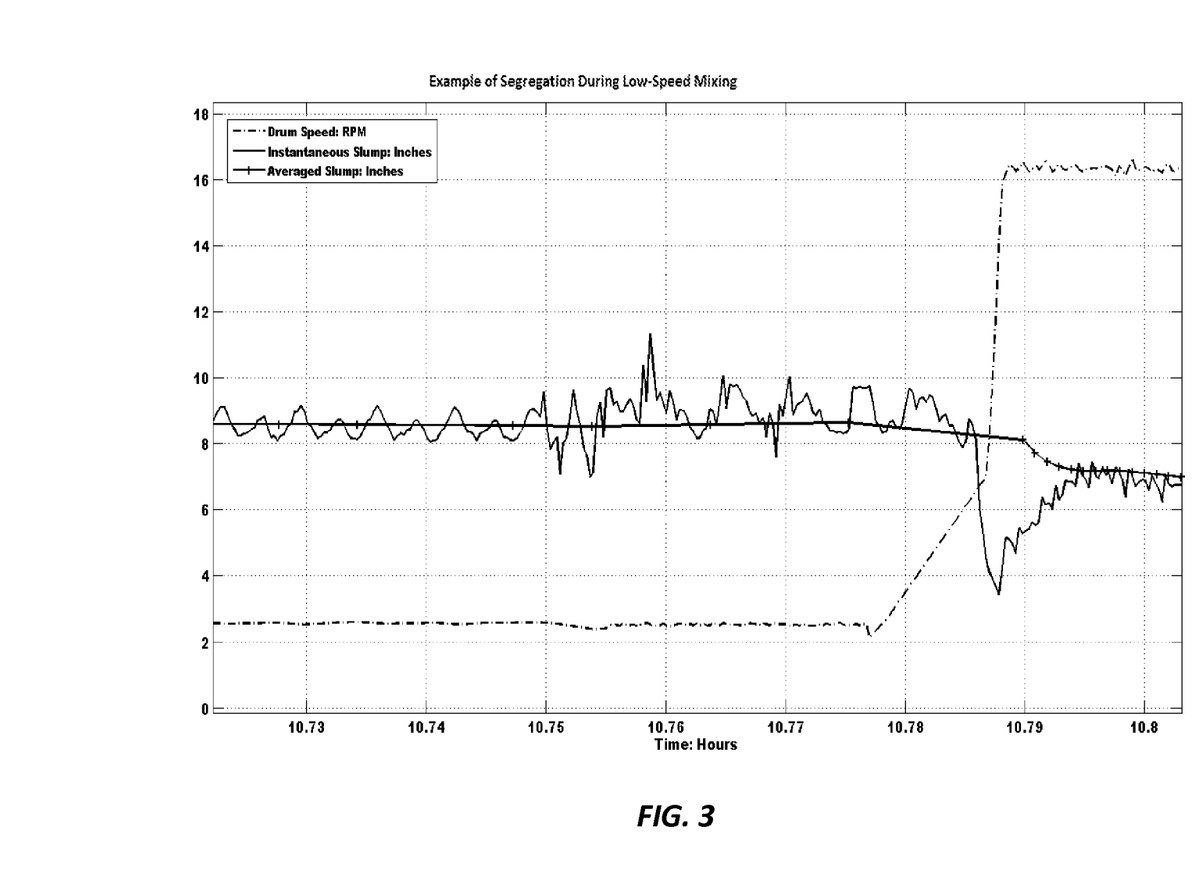
FIG. 3 is a graphic illustration of instantaneous slump and averaged slump behavior of a concrete which begins to segregate (at around 10.75 hours), wherein instantaneous slump values demonstrate a sudden shift from regular (small) variations in the periodic waveforms to highly irregular and extremely large wave variations that do not appear periodic in nature, and drum speed (RPM) is increased from a lower rotational speed to a higher rotational speed, and both instantaneous and average slump are both shown dropping but with different graphically represented behaviors.
Figure 4:
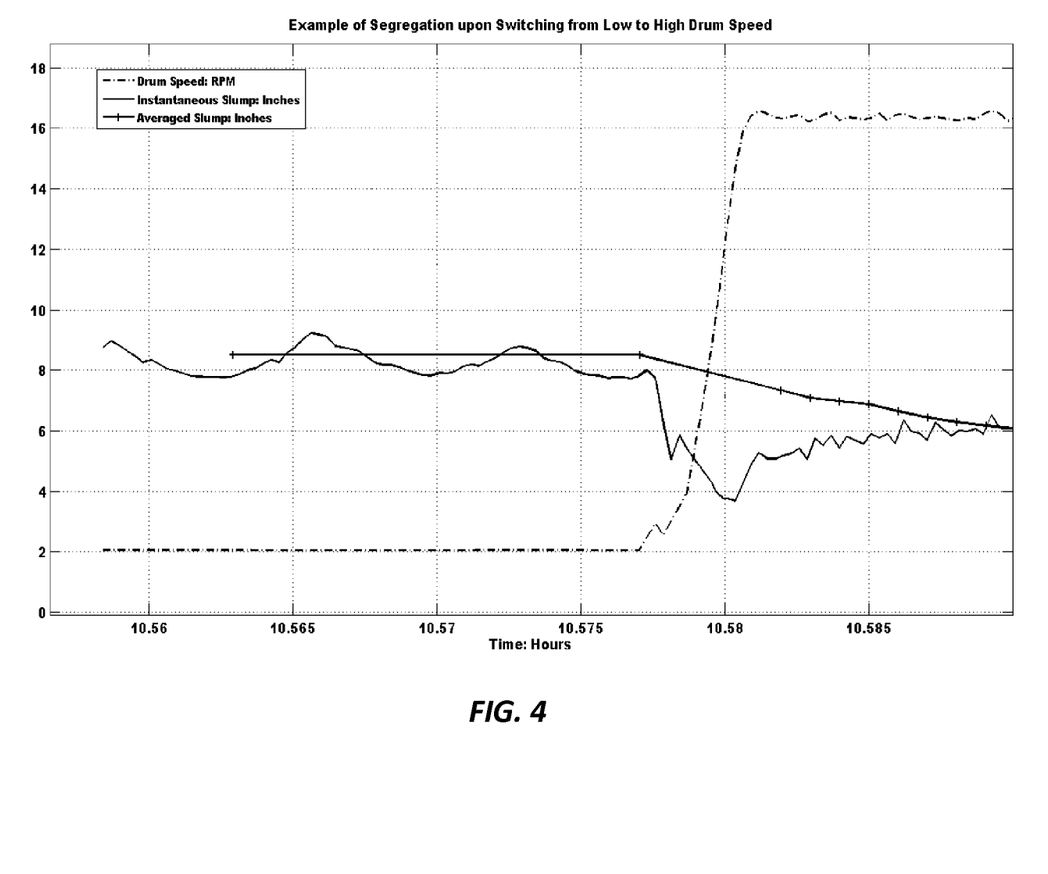
FIG. 4 is another graphic illustration of instantaneous slump and averaged slump behavior of a segregating concrete, wherein instantaneous slump (inches) is shown to drop precipitously after change of the drum speed from a lower rotational speed to a higher rotational speed, and to settle at a slump value that appears significantly lower than the slump value detected during the lower rotational speed, and further wherein the averaged slump value is also shown to drop to the same or similar value as the instantaneous slump value although at a slower change rate.

In exemplary systems and methods of the invention, the processor unit 6 is instructed or programmed to detect and to confirm dynamic segregation phenomena. As shown in FIGS. 3 and 4, instantaneous slump values and averaged slump values are plotted as an example of concrete which is demonstrating segregation during mixing. The present inventors believe that these instances of instantaneous and averaged rheological behavior in segregating concrete, as illustrated in FIGS. 3 and 4, demonstrate a drastic departure from the regular (i.e., small variations) behavior of non-segregated concrete (as illustrated in FIG. 2).

Dynamic segregation within concrete transported by delivery truck is not readily discerned by the human eye because the mixer drum is large and not typically illuminated. A portion of the wet concrete usually needs to be removed from the drum and poured onto a flat surface to be visually inspected for segregation (which can be seen where an excess of water bleeds on the upper surface or aggregates appear to clump within the mixture, or by other means). But the inventors also surprisingly discovered that such segregation can be detected and confirmed using the "jump speed" protocol and optional "constant speed" protocol, based on monitoring the concrete in the rotating drum to detect when averaged rheological behavior departs from usual non-segregated concrete behavior at constant speed and further to detect when instantaneous rheological behavior departs from usual non-segregated concrete behavior upon and immediately after a jump in speed of at least plus or minus four RPM, such that dynamic segregation may be detected and confirmed (using both "constant speed" and "jump speed" protocols) without having to remove the particular concrete mix from the drum.

Accordingly, as shown in FIG. 3, the instantaneous slump of concrete in a rotating mix drum is shown at the onset of a segregation event which begins around 10.75 hours (time is shown along the horizontal axis). The periodic waveforms corresponding to the instantaneous slump of the concrete mix in the period before 10.75 hours has only small variations between the periodic waveforms; but, beginning at 10.75 hours, the periodic curves suddenly acquire highly irregular and extremely large variations that are not periodic in nature, especially when compared to averaged slump readings. The irregularity becomes more pronounced when drum speed (RPM) is increased from about 2.4 RPM to about 16.2 RPM). After this period, drops in both the instantaneous slump and averaged slump values can be seen in the graph of FIG. 3. The drop in instantaneous slump is dramatic (between 10.78 and 10.79 hours); while the drop in the averaged slump value is more gradual during this same time period due to the averaging protocol implemented.

FIG. 4 is another graphic illustration of instantaneous slump and averaged slump of segregating concrete in a rotating mix drum during a dynamic segregation event. The behavior of the instantaneous slump before the speed change at 10.5755 is somewhat less chaotic (as the periodic waveforms appear more regular when compared to the wave forms for the pre-jump-speed-change period shown in FIG. 3). However, the instantaneous slump as shown in FIG. 4 appears to drop precipitously after a jump in drum speed (from 2 to over 16 RPM), and then gradually rises to meet the averaged slump, which meanwhile has dropped to a value which is similar or identical to the instantaneous slump value, though both instantaneous slump and averaged slump appear to have settled at a slower rate compared to the period before the speed jump.

As previously mentioned, it is possible that degradation to the continuity or smoothness of the instantaneous rheology (e.g., slump) behavior in the concrete during a segregation event is detected by the system processor regardless of whether the change in drum rotation rate is from a lower speed to higher speed (as illustrated in FIGS. 3 and 4) or from a higher speed to a lower speed. The behavior of the instantaneous slump and averaged slump in the latter case of dynamic segregation, wherein the speed jump is made from a higher to lower drum rotation speed, would likely resemble FIGS. 3 and 4 if either of these were viewed upside down in a mirror, for in such an opposite case the instantaneous slump and averaged slump of the concrete would appear to travel in the opposite direction if the drum speed were decreased rather than increased. In other words, if drum speed were decreased during the speed jump (and thus in a direction opposite to what is seen in FIGS. 3 and 4), the present inventors believe that instantaneous slump would be seen to spike upwards suddenly and then surge downward suddenly, while the averaged slump signal be seen (if represented in graphic form) to slope upwards in a more gradual manner over time as compared to the behavior of the instantaneous slump signal.

Figure 5:
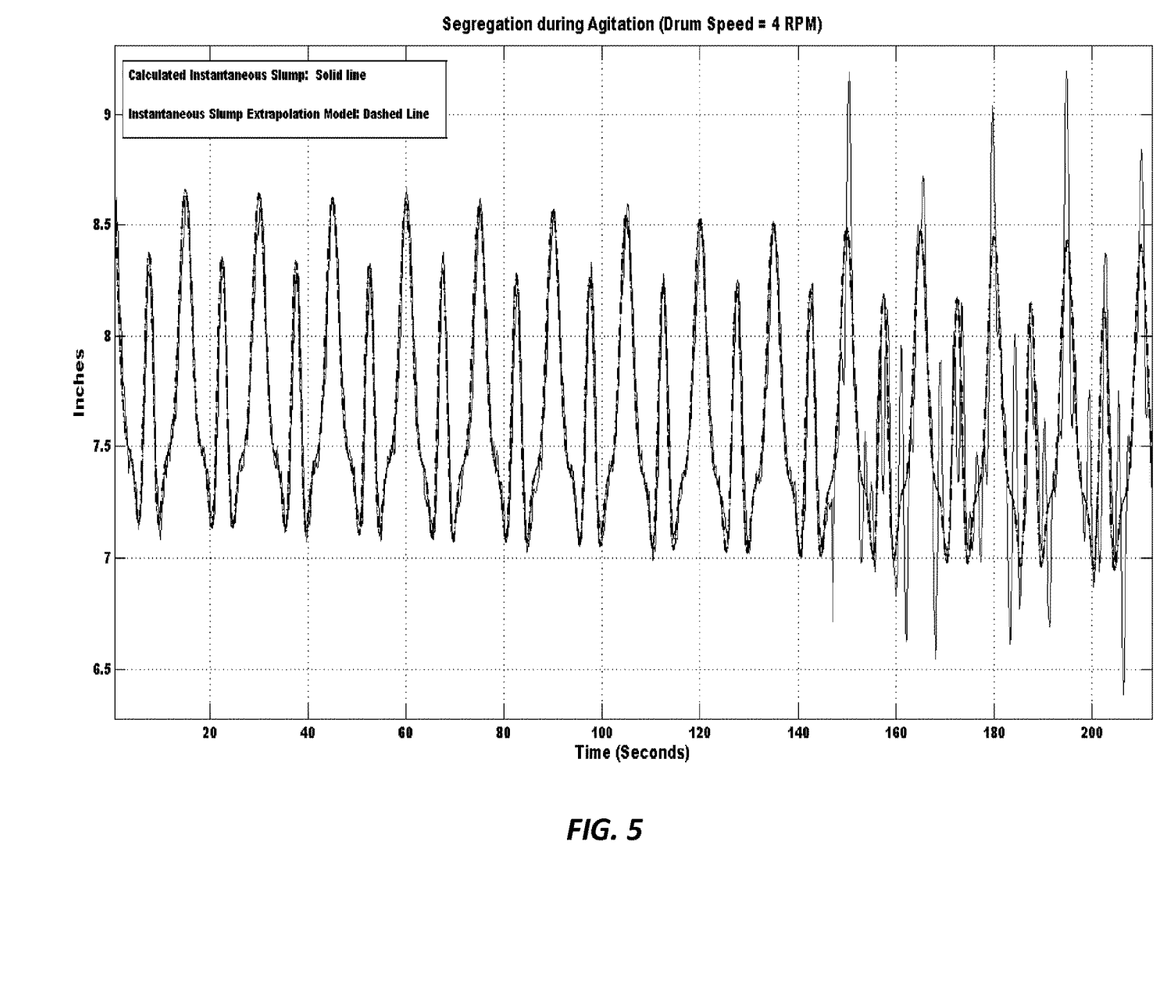
FIG. 5 is a graphic illustration of slump (inches along vertical axis) over time (seconds along horizontal axis) of a segregating concrete in a rotating mix drum rotating at about 4 RPM, wherein instantaneous slump of the concrete is represented as a regular periodic signal that departs from periodic behavior to assume a highly irregular behavior (shown as larger excursions in waveforms illustrated using solid lines beginning at around 150 seconds), wherein the dashed line represents an extrapolation of the periodic behavior.

As shown in FIG. 5, the instantaneous slump of concrete being rotated in the mixer drum at an agitation speed (~4 RPM) is monitored by the slump monitoring system, and the system processor is programmed to detect when the signal (derived from the hydraulic sensor and represented as the corresponding instantaneous slump) begins to depart from periodic behavior and subsequently to assume a highly irregular behavior. Thus, FIG. 5 illustrates an example of what happens during a dynamic segregation event beginning to occur at around 150 seconds, whereupon the instantaneous slump as calculated by the monitoring system processor (and depicted by the solid plotted graph line in FIG. 5) begins to display large excursions in the periodic waveform which depart drastically from the immediately preceding waveform pattern, after 150 seconds. This periodic pattern prior to segregation provides modeling information from which the expected future behavior is extrapolated, such that the system processor can be programmed to monitor behavior of non-segregating concrete, and to extrapolate data to generate a model of expected behavior, and such that the system processor can also select and/or modify (hence the term "pre-selected") a threshold or limit beyond which the system can detect rheological behavior which departs from the monitored/extrapolated behavior and which constitutes a detection of a potential segregation event that then trigger the system processor to initiate (or to complete) the one or more dynamic segregation protocol(s) as described herein.

Figure 6:
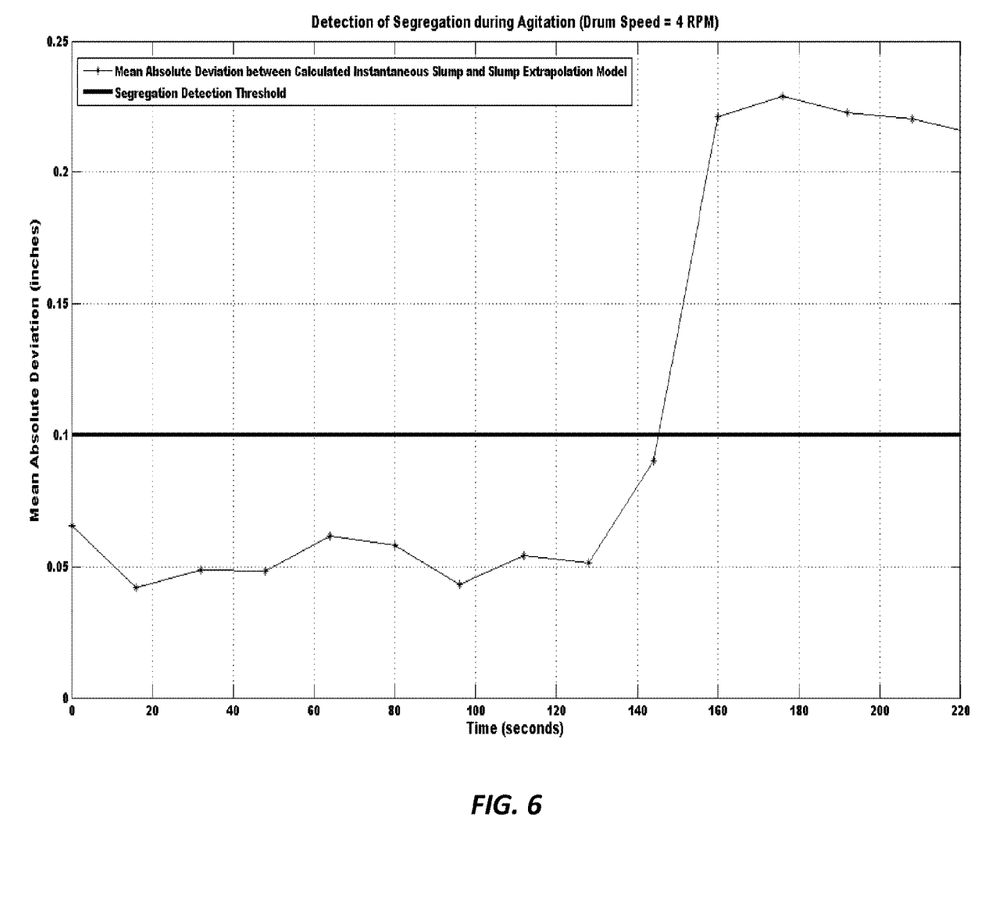
FIG. 6 is a graphic illustration of the mean absolute deviation (MAD) of slump behavior derived from segregating concrete in FIG. 5 and an illustrated threshold limit of 0.1 inches, which could serve as an example of the Constant Speed Departure Value ("CSDV") described in the present specification, for detecting segregation (as represented by the horizontal line at 0.1 inches) within the concrete being rotated at a relatively slow rotation speed.

As shown in FIG. 6, the mean absolute deviation (MAD) of instantaneous slump of the segregating concrete is calculated, and a represented threshold of 0.1 inches is used in the monitoring system processor for detecting the onset of a dynamic segregation state. The mean absolute deviation value is represented in FIG. 6 as a horizontal line signifying a trigger threshold. Crossing this threshold means that instantaneous slump has deviated more than 0.1 inches from the averaged slump for the same time period. A threshold crossing will then be sufficient to trigger an alarm and/or to initiate a system procedure whereby the mixer drum speed is changed from lower (e.g., agitation) speed to a higher (e.g., mixing) speed. The instantaneous slump and averaged slump estimates can then continue to be monitored immediately upon and after a jump in drum speed (e.g., at least plus or minus 4 RPM difference or greater). The rheology monitoring system is programmed to ascertain whether the rheology (e.g., slump) of the concrete displays different degradation (in continuity or smoothness) behaviors of the instantaneous slump and the averaged slump in the concrete as illustrated in FIGS. 3 and 4.

Two Separate Protocols for Detecting Dynamic Segregation.

As previously summarized, the present invention provides a system and method for detecting dynamic segregation events in concrete, by employing two protocols: (A) one protocol for detecting dynamic segregation upon and immediately after a "jump" in mixer drum rotation speed of at least plus or minus four RPM or more; and (B) another protocol for detecting dynamic segregation at "constant" mixer drum rotation speed.

For each protocol, the system and methods of the invention employ threshold values or limits which will be used by the automated monitoring system processor to determine when a segregation event has occurred for the given protocol, so that an alarm or indication (visual and/or audible) can be provided to a driver or operator such that the other protocol can be initiated. Although the "jump speed" protocol is considered to be of primary importance by the present inventors, while the "constant speed" protocol is considered to be optional, it may be preferable to employ both protocols to attain a higher degree of assurance that dynamic segregation has occurred.

As the definition of "jump speed" is based on a sufficiently large change in the "constant speed," it perhaps makes sense to start discussion of the Constant Speed Departure Value (Protocol B). The term "Constant Speed Departure Value" or "CSDV" as used herein shall mean and refer to a value for purposes of helping to define during implementation of Protocol A when the instantaneous rheology (e.g., slump) value of concrete in a drum being rotated at a constant speed (for at least three successive drum rotations) demonstrates an unacceptable departure (e.g., an extremely large excursion in the instantaneous slump reading in real time) when compared to the expected (or extrapolated or modeled) behavior of the concrete being monitored in a non-segregated state. As previously mentioned, the CSDV is preferably calculated and/or modified by the system processor, and this could be based on various factors such as concrete mix design, temperature of the concrete, performance, and other factors.

An exemplary CSDV may be generated as follows. If the rheological parameter (e.g., slump) of the concrete is expressed by the function $Y(t)=F(R(t), P(t))$, where $R(t)$ and $P(t)$ are the drum speed and hydraulic pressure, respectively, at time t, then segregation at a constant drum speed is found to be associated with a departure of $Y(t)$, from the expected (modeled) normal (non-segregated) periodic behavior, to an irregular and much less predictable behavior that persists over multiple drum rotations at constant speed, unless corrective measures are taken to reverse the segregation state of the concrete in the drum. The departure from the expected (or modeled) normal behavior of the concrete in the drum can be quantified and detected using various mathematical methods. One such method is described here (and graphically illustrated in FIGS. 5 and 6) using slump as an example of one particular concrete rheology parameter that is monitored by the system. The methodology can be applied as well to other rheological parameters, as previously explained. One may employ standard time series methodologies such as Fourier series decomposition and trend analysis to develop an accurate model $Z(t)$ of the rheological parameter $Y(t)$ when Y is regular and periodic and the drum is rotating at a constant speed. Thus, rheological parameter $Y(t)$ is monitored so that $Z(t)$ can be calculated to obtain the expected value of the rheological parameter in the absence of segregation in the concrete. Then, to detect segregation, the system is programmed such that, after each complete revolution of the mixer drum at a constant speed (e.g., at agitation or mixing speed, or somewhere in between), the mean absolute deviation of Y from Z can be calculated, such as in accordance with formula (1), as provided below:

$$MAD(r) = \frac{1}{T}\int_{t_r}^{t_r+T} |Y(\tau) - Z(\tau)| d\tau \qquad (1)$$

wherein $t_r$ indicates the beginning time of drum revolution r, and T represents the period of the drum rotation, so that the integral calculation is performed over complete drum rotations. If it is found that $MAD(r)>D$ for several consecutive rotations (preferably, at least two successive complete rotations, and more preferably, at least three successive complete rotations), where D is a threshold that depends on the particular rheological parameter being monitored, then segregation can be deemed to have occurred.

Hence, the system processor may be programmed to generate and/or to modify the Constant Speed Departure Value (CSDV) for detecting dynamic segregation events. It is preferred that the processor be programmed to do this, rather than relying on an operator or driver to input an arbitrary threshold or limit value, as the processor can be programmed to consider various factors, such as concrete mix design and raw materials information, temperature of the concrete, heat of the concrete, nature and amount of chemical admixture or water used, and other factors perhaps too numerous to mention summarily. The system processor can also be programmed to take into account historical performance data, and to make adjustments or corrections based on previous batch histories or environmental or circumstantial changes occurring within the same batch delivery.

Confirmation of dynamic segregation can be done empirically by stopping the drum when the system processor detects that a Constant Speed Departure Value (CSDV) is met (i.e., a pre-selected limit or CSDV is satisfied or exceeded). That segregation occurs in concrete when such CSDV limit is met has been confirmed by the present inventors through the inspection and photographing of concrete discharged from the mixer drum. In actual practice, the integral in equation (1) set forth above can be approximated by a finite sum over the discrete times during which the signal Y is sampled, and the sampling frequency will depend on the rotation speed of the drum. A sampling of 10 to 50 uniformly spaced points in time per drum rotation should be sufficient, and a sample of 50 to 100 uniformly spaced points in time per drum rotation is more preferred.

The term Jump Speed Departure Value (JSDV) for Protocol A, on the other hand, means and refers to a threshold or limit for purposes of helping to define when the averaged rheology (e.g., slump) value, and optionally the instantaneous rheology value, or both, of the concrete upon and immediately after the jump in drum rotation speed (by at least plus or minus four 4 RPM, more preferably at least plus or minus six RPM and most preferably at least plus or minus eight 8 RPM difference) departs from the rheological behavior displayed before the speed jump.

In preferred embodiments, the system processor is programmed to monitor the averaged rheology (e.g., slump) value to determine whether the JSDV limit is met (i.e., satisfied or exceeded). As shown in FIG. 3, the averaged slump value upon and immediately after the speed jump (occurring between 10.77 and 10.78 hours) began to change such that by the time the jump was completed, and the drum was rotated at a changed constant speed (just before 10.79 hours), the averaged slump was clearly shown as changing after the drum speed jump; and at this point the processor is programmed to determine when the JSDV limit is met.

FIG. 4 graphically illustrates dynamic segregation behavior somewhat similar to FIG. 3. At around 10.578 hours in FIG. 4, when the speed jump (increase) is initiated, the averaged slump change (decrease) begins; such that by 10.69 hours, after the speed change is completed and the constant drum speed is now 16 RPM, the averaged slump has noticeably fallen (by at least two inches in slump).

The present inventors believe that a Jump Speed Departure Value (JSDV) can be optionally used when monitoring the instantaneous slump, and detecting when it demonstrates spiking behavior immediately upon and after (during successive drum rotations) the drum speed change (also as shown in FIGS. 3 and 4). However, it is preferable to focus on the change in averaged slump and to select a threshold value based on a change in averaged slump, because one must also take into consideration various other parameters that could affect the overall change in instantaneous rheology (e.g., slump, slump flow) such as concrete design mix, truck equipment type (e.g., drum dimensions and/or geometry, blade configuration, truck hydraulic system for rotating drum).

When the concrete rheology monitoring system processor is programmed to monitor the averaged rheology value to detect when the JSDV limit is met, this JSDV is more precisely designated as the "JSDV(A)". The system processor is optionally programmed to monitor instantaneous rheology value to detect when the JSDV limit is met, and this is more precisely designated as the "JSDV(I)".

The programming of a concrete monitoring system processor to determine when rheology meets or exceeds a JSDV(A) limit in the case of averaged rheology monitoring and/or a JSDV(I) limit in the case of instantaneous rheology monitoring is unprecedented. The present inventors were indeed surprised during experimental testing when they discovered some instances wherein a dosing of plasticizing chemical admixture into the concrete, and then jumping the drum speed (in this case from an agitation to mixing speed) resulted in a detected slump decrease rather than an increase in slump (as one would otherwise be led to expect in a non-segregating concrete). They confirmed empirically, upon removing the concrete from the mixer drum, that segregation was responsible for this strange scenario.

A threshold or limit value in terms of the JSDV(A) limit for detecting segregation while monitoring averaged rheology (in Protocol A) is preferably selected or modified by the system processor, or, alternatively selected by the user or operator, as follows. If $t_0$ represents time just prior to the jump in drum rotation speed from a first constant rotation speed to a second constant rotation speed (where the difference is at least 4 plus or minus RPM) and if θ represents the extent of a time window such that by time $t_0+\theta$, the mixer drum has undergone several complete rotations at a first constant rotation speed and more preferably for at least two or three complete rotations after initiation of the speed jump, then dynamic segregation may be said to occur (or the JSDV(A) limit is otherwise said to be met) as a mathematical proposition, as illustrated in formula 2 below, where $$\text{Min}_{\{0<\tau<\theta\}} |Y(t_0+\tau)-Y(t_0)| > M, \quad (2)$$

wherein M represents a threshold value set for the particular rheological parameter being monitored, and other factors that could lead to such a change in the rheological parameter have been accounted for.

A threshold or limit value in terms of the JSDV(I) can similarly be derived or modified by the system processor based on formula 2 above. However, the selection and use of the JSDV(I) limit is optional and less preferred relative to the use of the JSDV(A) limit, because the present inventors believe that the behavior of the instantaneous rheology (e.g., slump) value seen in the graphs of FIGS. 3 and 4 for example is rather erratic and thus less reliable (in terms of the behavior over time) for indicating dynamic segregation is occurring; it may be more difficult, moreover, to derive a JSDV(I) limit and/or for the system to detect that this limit is met base on instantaneous rheology monitoring due to possibly proportionally larger effects that factors such as mixer drum and drum blade shape and concrete temperature may have on the overall rheology of the concrete as it moves over the blades during drum rotation. The present inventors believe, nevertheless, that JSDV(I) detection can be used as an additional tool to confirm dynamic segregation and to provide added assurance that further steps need to be taken when the JSDV(A) limit is detected to be met. Hence, further exemplary systems and methods of the present invention will involve the processor detecting when both the JSDV(I) limit and the JSDV(A) limit are met.

Figure 7:
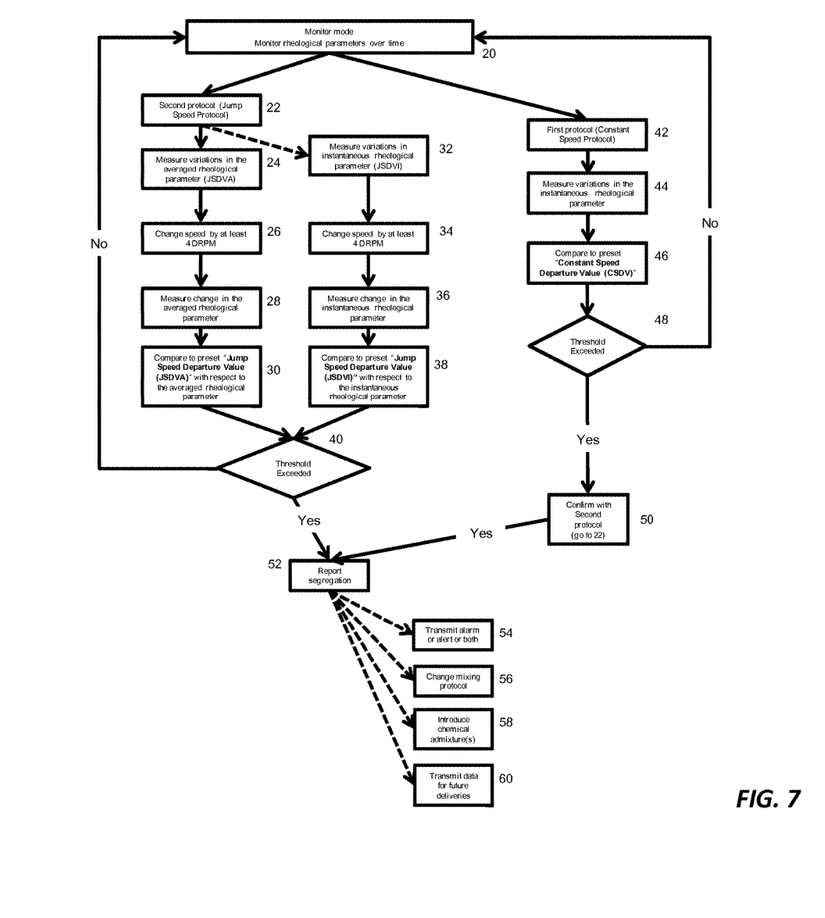
FIG. 7 is a flow chart of an exemplary system and method of the present invention which implements a constant speed protocol and a jump speed protocol for detecting and confirming the existence of dynamic segregation in a concrete contained in a mixer drum.

A flow chart (block diagram) is provided in FIG. 7 to illustrate an exemplary system and process of the present invention. The system processor is programmed to monitor one or more rheological parameters (e.g., slump, slump flow, yield stress, and/or viscosity) continuously for a particular period in time (designated at 20), and programmed to implement one or more protocols for detecting dynamic segregation during continuous monitoring.

As shown in FIG. 7, the first protocol for monitoring for and detecting when dynamic segregation has occurred is referred to as a "jump speed" protocol (as designated at block 22.) The first protocol (designated at blocks 22/24/26/28/30) involves the system processor in monitoring the averaged rheological (e.g., slump) parameter values (as designated at 24) of the concrete in the rotating mixer drum. The processor is programmed to monitor and to detect, upon a sudden change (by the truck driver or system processor) of drum rotation speed, e.g., a jump or sudden increase or decrease by at least plus or minus four RPM (as designated at 26), and thus monitors the change in the averaged rheology value (as designated at 28) to determine if a Jump Speed Departure Value or "JSDV(A)" is met (i.e., satisfied or exceeded) (as designated at 30).

If the system determines that JSDV(A) is met (or exceeded) (as designated at block 40 in FIG. 7), then the system processor is programmed to perform one or more operations to indicate or report that dynamic segregation is detected (as designated at 52).

In further exemplary embodiments, the system processor is programmed to run an additional dynamic segregation detection procedure within the first protocol, either simultaneously with or subsequently to the procedures outlined in blocks 24-30 of FIG. 7). These exemplary additional steps involve monitoring variations in the instantaneous rheological parameter (beginning with block 32 of FIG. 7). Once the drum speed is changed suddenly by at least plus or minus four RPM (as designated at 34), the system processor monitors for changes in the instantaneous rheology parameter (as designated at 36), to detect whether there is a change that meets the Jump Speed Departure Value for the instantaneous rheology value being monitored as designated at 38 (the "JSDV(I)"). If the JSDV(I) limit is determined to be met (as designated at block 40), then the system processor is programmed to initiate at least one operation to indicate or report that detected dynamic segregation is detected (as designated at block 52).

If either of the pathways under the first protocol, beginning at block 22 and extending through 24/26/28/30 and 32/34/36/38, results in the respective Jump Speed Departure Value not being met, the system processor is programmed (as designated in block 40) to return to monitoring mode (as designated in block 20).

The system processor is programmed to initiate a second protocol, otherwise termed the "constant speed" protocol which begins at block 42 and involves various steps and software programming functions represented in blocks 42 through 50. At a constant mixer drum speed (and after at least two complete drum rotations and preferably at least three complete drum rotations), the system processor monitors an instantaneous rheology (e.g., slump) value (as designated at 44), and compares the instantaneous rheology value to a pre-set Constant Speed Departure Value (CSDV) (as designated at 46). The processor is programmed, if CSDV is determined not to be met, to return to monitoring mode (designated at 20) so that the first protocol (22) or second protocol (42) can be revisited subsequently. If the system detects that CSDV is met (as designated at 50), the processor is instructed to take action that will lead to confirmation of dynamic segregation through implementation of the first protocol (22).

While FIG. 7 diagrammatically illustrates an exemplary system and process wherein the first (jump speed) protocol can be assumed to be implemented first and the second (constant speed) protocol is assumed to be implemented subsequently; however, it is possible for the system processor to implement the second protocol first (42-50) and to implement the first protocol (22-40) subsequently, as discussed above.

One may therefore program the system process to confirm dynamic segregation using both protocol, so as to obtain added assurance before implementing an alarm, reporting, or corrective action. For example, the system can (i) send of an alarm or other indication (whether audible or visual or electrical) to the concrete mix plant, a dispatch center, an operator of the concrete delivery truck, or to some or all of these, to indicate that segregation is detected (54); (ii) implement further mixing to mitigate segregation of concrete (56); (iii) cause at least one chemical admixture to be introduced into the concrete-containing mixer drum for mitigating segregation of the concrete (58); (iv) transmit data to a dispatch center, concrete mix plant, or other remote site, so that the concrete mix plant can be alerted to adjust the concrete mix design or prepare the concrete mix to avoid segregation in subsequent delivery runs (60); or (v) any combination or all of the foregoing. For (iv), the data transmitted to the dispatch center can include the monitored instantaneous and averaged rheology values, including where the CSDV and JSDV(A) limits were met or exceeded.

In further exemplary embodiments, the system may be programmed to monitor and to transmit data, as described for subparagraph (iv) above, for both averaged and instantaneous rheology values upon and after a speed jump; and, in still further exemplary embodiments, the system may also be programmed to monitor and to transmit data regarding where CSDV limits for both low and high speed were met or exceeded, to provide more detail helpful for adjusting the concrete mix (as described in subparagraph iv above); or, as another example, to make a selection from chemical admixtures (such as one or more viscosity modifying agents) that could be introduced into the concrete (as described in subparagraph iii above).

It is contemplated that conventional viscosity modifying agents (VMAs) can be employed in "iii" as referenced above. These VMAs include but are not limited to: (a) associative thickeners selected from the group consisting of hydrophobically modified alkali swellable acrylic copolymer, hydrophobically modified urethane copolymer, associative thickeners based on polyurethanes, cellulose, polyacrylates, polyethers, and mixtures thereof; (b) marine gums selected from the group consisting of algin, agar, carrageenan, and derivatives and mixtures thereof; (c) plant exudates selected from the group consisting of locust bean, gum arabic, gum Karaya, tragacanth, Ghatti, and derivatives and mixtures thereof; (d) seed gums selected from the group consisting of guar, locust bean, okra, psyllium, mesquite, and derivatives and mixtures thereof; (e) starch-based gums selected from the group consisting of ethers, esters, and derivatives and mixtures thereof (See e.g., U.S. Pat. No. 6,110,271 at Column 3, lines 38-46); (f) biopolymer polysaccharides selected from the group consisting of welan gum, diutan (S-657), xanthan, rhamsan, gellan, dextran, pullulan, curdlan, and derivatives and mixtures thereof; and mixtures of any of the foregoing VMAs.

The present invention is described herein using a limited number of illustrative embodiments not intended to limit the scope of the invention as otherwise described and claimed herein. Modifications and variations from the described embodiments can exist. It should be understood that the invention is not limited to the specific details set forth above.

What is claimed is:

1. A concrete monitoring system for detecting dynamic segregation in a concrete mix contained in a rotatable mixer drum, the drum having an inner wall with at least one blade spirally-mounted on the inner wall for agitating or mixing the concrete during mixer drum rotation, the system comprising:

a system processor programmed to monitor at a rate of at least ten times per drum rotation at least one rheology parameter of concrete contained in a rotating drum by measuring the energy or hydraulic pressure required for rotating the concrete-containing drum as a function of time and thereby to obtain an instantaneous value for the rheology parameter ("instantaneous rheology value"), the processor programmed to average the monitored rheology values for the rheology parameter in question over a period of time to obtain an averaged value for the rheology parameter ("averaged rheology value");

the system processor further programmed to deploy both a first dynamic segregation detection protocol to detect dynamic segregation based on the averaged rheology value and a second dynamic segregation detection protocol to detect dynamic segregation based on the instantaneous rheology value, wherein:

(A) the first dynamic segregation detection protocol comprises:

monitoring the concrete rheology parameter before and after drum rotation is detected to jump from a first constant rotation speed to a second constant rotation speed, wherein the difference between the first and second rotation speeds is at least plus or minus four drum rotations per minute; and, upon completion of the jump, detecting when a change in the averaged rheology value meets or exceeds a Jump Speed Departure Value that is pre-selected with respect to the monitored averaged rheology value ("JSDV(A) limit");

(B) the second dynamic segregation detection protocol comprises:

monitoring the concrete while the mixer drum is rotating at a constant rotation speed and detecting when a change in the monitored instantaneous rheology value meets or exceeds a Constant Speed Departure Value ("CSDV limit"); and the system processor further programmed, upon or after detecting that the JSDV(A) limit and the CSDV limit are met or exceeded, to initiate at least one of the following:

(i) sending of an alarm or indication to a concrete mix plant, a dispatch center, an operator of the concrete delivery truck, or to some or all of these, to confirm that segregation is detected;

(ii) changing of mixer drum rotation rate;

(iii) introducing at least one chemical admixture into the concrete-containing mixer drum for mitigating segregation of the concrete;

(iv) transmitting of data to a dispatch center, concrete mix plant, or other remote site for adjusting concrete mix design in subsequent concrete batches; or (v) performing any combination or all of the foregoing; and wherein the system processor is electrically or electronically connected to a sensor for sensing rotational speed of motor or hydraulic pressure drive used for rotating the concrete mixer drum.

2. The concrete monitoring system of claim 1 wherein the mixer drum is mounted on a concrete delivery truck.

3. The concrete monitoring system of claim 1 wherein the first dynamic segregation detection protocol further comprises detecting when a change in the instantaneous rheology value meets or exceeds a Jump Speed Departure Value preselected with respect to the monitored instantaneous rheology value ("JSDV(I) limit").

4. The concrete monitoring system of claim 3 wherein the system processor detects that both JSDV(A) and JSDV(I) limits in the first dynamic segregation detection protocol are met or exceeded.

5. The concrete monitoring system of claim 1 wherein the system processor is programmed to implement both first and second dynamic segregation detection protocols in either order.

6. The concrete monitoring system of claim 1 wherein the rheology parameter of the concrete being monitored is at least one of slump, slump flow, yield stress, and viscosity.

7. The concrete monitoring system of claim 1 wherein the rheology parameter of the concrete being monitored is slump or slump flow.

8. The concrete monitoring system of claim 1 wherein the system processor is programmed to monitor concrete in the mixer drum at a constant rotation speed, and, upon detecting that the CSDV limit is met, to initiate a signal to prompt an operator of the concrete delivery truck upon which the rotating concrete mixer drum is mounted, to change the constant rotation speed of the mixer drum from a first constant rotation speed to a second constant rotation speed, whereby the difference between the first and second constant rotation speeds is at least plus or minus four rotations per minute.

9. The concrete monitoring system of claim 1 wherein the system processor is programmed to monitor concrete in the mixer drum rotated at a first constant rotation speed of 1 to 6 rotations per minute, and, upon detecting that the CSDV limit is met, to initiate a signal to prompt an operator of the concrete delivery truck to change the constant rotation speed to a second constant rotation speed between 10 to 20 rotations per minute.

10. The concrete monitoring system of claim 1 wherein the system processor is programmed to monitor concrete in the mixer drum rotated at a first constant rotation speed of 10 to 20 rotations per minute, and, upon detecting that the CSDV limit is met, to initiate a signal to prompt an operator of the concrete delivery truck to change the constant rotation speed to a second constant rotation speed between 1 to 6 rotations per minute.

11. The concrete monitoring system of claim 1 wherein the system processor implements the first dynamic segregation detection protocol "A" upon detecting that the CSDV limit is met and implements the second dynamic segregation detection protocol "B" upon detecting that the JSDV(A) limit is met.

12. The concrete monitoring system of claim 1 wherein the system processor is further programmed to monitor, upon change in mixer drum rotation speed of at least plus or minus four rotations per minute, the instantaneous rheology parameter of the concrete and to detect when the instantaneous rheology value meets or exceeds the JSDV(I) limit.

13. The concrete monitoring system of claim 1 wherein, in the second dynamic segregation detection protocol "B", the system processor is programmed to send an alarm or indication to the operator of the mixer drum to change the constant rotation rate of the drum by at least plus or minus six drum rotations per minute.

14. The concrete monitoring system of claim 1 wherein the system processor is programmed to introduce at least one chemical admixture into the concrete contained in the drum after or upon detecting that the CSDV limit and JSDV(A) limit are met or exceeded.

15. The concrete monitoring system of claim 1 wherein the system processor is programmed to transmit data relating to protocols A and B to a dispatch center or ready-mix plant after or upon detecting that the CSDV limit and JSDV(A) limit are met or exceeded.

16. A process for detecting and confirming dynamic segregation in a concrete mix contained in a rotatable mixer drum mounted on a concrete delivery truck, the drum having an inner wall with at least one blade spirally-mounted on the inner wall for agitating or mixing the concrete during rotation, the process comprising:
monitoring at a rate of at least ten times per drum rotation at least one rheology parameter of concrete contained in a rotating drum by measuring the energy or hydraulic pressure required for rotating the concrete-containing drum as a function of time and thereby obtaining instantaneous values for the rheology parameter ("instantaneous rheology values"), and averaging the monitored rheology values for the rheology parameter in question over a period of time to obtain an averaged value for the rheology parameter ("averaged rheology values");
implementing both a first dynamic segregation detection protocol to detect dynamic segregation based on averaged rheology values and a second dynamic segregation detection protocol to detect dynamic segregation based on instantaneous rheology values, wherein
(A) the first dynamic segregation detection protocol comprises:
monitoring the concrete rheology parameter before and after drum rotation is detected to jump from a first constant rotation speed to a second constant rotation speed, wherein the difference between the first and second rotation speeds is at least plus or minus four drum rotations per minute; and,
upon completion of the jump, detecting when a change in the averaged rheology value meets or exceeds a Jump Speed Departure Value that is pre-selected with respect to the monitored averaged rheology value ("JSDV(A) limit");
(B) the second dynamic segregation detection protocol comprising:
monitoring the concrete while the mixer drum is rotating at a constant rotation speed and detecting when variations in the monitored instantaneous rheology values meet or exceed a Constant Speed Departure Value ("CSDV limit"); and
initiating at least one of the following upon or after confirming that the JSDV(A) limit and the CSDV limit are met or exceeded;
(i) sending of an alarm or indication to a concrete mix plant, a dispatch center, an operator of the concrete delivery truck, or to some or all of these, to confirm that segregation is detected;
(ii) changing of mixer drum rotation rate;
(iii) introducing at least one chemical admixture into the concrete-containing mixer drum for mitigating segregation of the concrete;

(iv) transmitting of data to a dispatch center, concrete mix plant, or other remote site for adjusting concrete mix design in subsequent concrete batches; or (v) performing any combination or all of the foregoing; and wherein the system processor is electrically or electronically connected to a sensor for sensing rotational speed of motor or hydraulic pressure drive used for rotating the concrete mixer drum.

17. The process of claim 16 wherein the mixer drum is mounted on a concrete delivery truck.

18. The process of claim 17 wherein the first dynamic segregation detection protocols further comprises detecting when a change in the instantaneous rheology value meets or exceeds a Jump Speed Departure Value preselected with respect to the monitored instantaneous rheology value ("JSDV(I) limit").

19. The process of claim 18 wherein the system processor detects that both JSDV(A) and JSDV(I) limits in the first dynamic segregation detection protocol have been met or exceeded.

20. The process of claim 16 wherein the rheology parameter of the concrete being monitored is at least one of slump, slump flow, yield stress, and viscosity.

21. The process of claim 16 wherein the rheology parameter of the concrete being monitored is slump or slump flow.

22. The process of claim 16 wherein concrete is monitored in a mixer drum at a constant rotation speed, and, upon detection that the CSDV limit is met, prompting an operator of a concrete delivery truck, upon which the rotating concrete mixer drum is mounted, to change the constant rotation speed of the mixer drum from a first constant rotation speed to a second constant rotation speed, the first and second constant rotation speeds having a difference of at least plus or minus four rotations per minute.

23. The process of claim 16 wherein concrete is monitored in a mixer drum rotated at a first constant rotation speed of 1 to 6 rotations per minute, and, upon detection that the CSDV limit is met, a system processor sends a signal to an operator of the concrete delivery truck to change the constant rotation speed of the mixer drum to a second constant rotation speed between 10 to 20 rotations per minute, and the system processor detects when at least the JSDV(A) limit is met or exceeded.

24. The process of claim 16 wherein concrete is monitored in a mixer drum rotated at a first constant rotation speed of 10 to 20 rotations per minute, and, upon detection that the CSDV limit is met, a system processor sends a signal to an operator of the concrete delivery truck to change the constant rotation speed of the mixer drum to a second constant rotation speed between 1 to 6 rotations per minute, and the system processor detects when at least the JSDV(A) limit is met or exceeded.

25. The process of claim 16 wherein a system processor is further programmed to implement both protocols A and B, whereby the system processor implements protocol (B) upon detecting that the JSDV(A) limit of protocol (A) is met or exceeded, and implements protocol (A) upon detecting that the CSDV limit of protocol (B) is met.

26. The process of claim 16 wherein the system processor is further programmed to monitor, upon change in rotation speed of at least plus or minus four drum rotations per minute, the instantaneous rheology parameter of the concrete and to detect when the instantaneous rheology value meets or exceeds the JSDV(I) limit.

27. The process of claim 16 wherein a system processor is programmed to initiate an alert or signal to the operator of the mixer drum to change the constant rotation rate of the drum by a decrease or increase of at least six rotations per minute.

28. The process of claim 16 further comprising introducing at least one chemical admixture into the concrete contained in the mixer drum after detecting that the JSDV(A) limit and the CSDV limit are met.

\* \* \* \* \*